United States Patent [19]

Kravetz et al.

[11] Patent Number: 4,651,000
[45] Date of Patent: Mar. 17, 1987

[54] METHOD FOR DETERMINING THE PERFORMANCE OF DETERGENTS IN THE REMOVAL OF PROTEINACEOUS SOILS

[75] Inventors: Louis Kravetz; William T. Shebs, both of Houston, Tex.; Atwood C. Page, Jr., Oakdale, Calif.

[73] Assignee: Shell Oil Company, Houston, Tex.

[21] Appl. No.: 727,488

[22] Filed: Apr. 26, 1985

[51] Int. Cl.$^4$ .................. G01T 1/167; G21H 5/02
[52] U.S. Cl. ............................. 250/303; 73/60.1
[58] Field of Search ................ 250/303; 73/60.1; 250/303

[56] References Cited

PUBLICATIONS

A. K. Phansalker, et al., A Tracer Method for Determination of Deposition of Carbon on Cotton, *J. Phys. Chem.*, vol. 59 (Sep. 1955) pp. 885–888.

M. Cooper, et al., Labeling Human Erythrocytes with Radiochromium, *J. Lab. & Clin. Med.*, vol. 47 (Jan. 1956), pp. 65–71.

N. C. H. Jones, et al., The Interpretation of Measurements with $^{51}$Cr-Labelled Red Cells, *Clinical Science*, vol. 15 (1956), pp. 207–218.

P. L. Mollison, The Use of the Isotope $^{51}$Cr as a Label for Red Cells, Brit. J. Haematology, vol. 1 (1955), pp. 62–74.

S. J. Gray, et al., The Tagging of Red Cells and Plasma Proteins with Radioactive Chromium, *J. Clin. Investig.*, vol. 29 (1950), pp. 1604–1613.

B. E. Gordon, et al., A Triply Labeled Particulate Soil for Detergency Study, *J. Am. Oil Chem. Soc.*, vol. 46 (Oct. 1969), pp. 537–543.

B. E. Gordon, et al., The Development of a Particulate Radioactive Soil for Detergency Studies, *J. Am. Oil Chem. Soc.*, vol. 45 (Nov. 1968) pp. 754–759.

W. T. Shebs, et al., Improvements in Detergency Precision with Radioactive Soils, *J. Am. Oil Chem. Soc.*, vol. 45 (May 1968) pp. 377–380.

B. E. Gordon, et al., A Double Label Radiotracer Approach to Detergency Studies, *J. Am. Oil Chem. Soc.*, vol. 44 (May 1967), pp. 289–294.

*Primary Examiner*—Bruce C. Anderson
*Assistant Examiner*—Jack I. Berman

[57] ABSTRACT

An improved method for determining the performance of detergents in the removal of proteinaceous soils, which centers upon the use as test soil of radiolabelled blood hemoglobin and upon the evaluation of detergency by both light reflectance and scintillation counting measurements. The method is particularly applicable to the determination of the performance of laundry detergent formulations containing enzymes.

4 Claims, No Drawings

METHOD FOR DETERMINING THE PERFORMANCE OF DETERGENTS IN THE REMOVAL OF PROTEINACEOUS SOILS

FIELD OF THE INVENTION

This invention relates to a method for determining the performance of detergent formulations. More particularly, this invention relates to a method of enhanced reliability and versatility for determining the performance of laundry detergent formulations in the removal of proteinaceous soils.

BACKGROUND OF THE INVENTION

As part of continuing efforts in the art to formulate high performance, cost-effective detergent products, it is necessary to obtain accurate and reproducible data for the performance of different detergent components and formulations in applications which call for the removal of different types of common soils. The reliability of methods available for the quantitative determination of soil removal is in many cases a limiting factor in these efforts. It is the object of this invention to provide a method having enhanced reliability and versatility for determining the performance of detergents in the removal of proteinaceous soils.

A number of methods are known and commonly used to measure soil removal in detergent performance studies. Of particular relevance to the present invention are methods which center upon measurements of light reflectance from clean, soiled, and laundered fabric swatches. Under such methods, reflectance is first measured for fresh, clean fabric swatches, then for swatches which have been soiled with controlled amounts of one or more soils, and finally for swatches which have been soiled and then laundered with the test detergent under controlled conditions. Comparison of the three sets of reflectance measurements provides a quantitative determination of the performance of the detergent. (Description of such reflectance tests are found, for example, in the text Detergency, vol. 5, part 1, Surfactant Science Series, edited by G. Culter and R. C. Davis, Marcel Dekker, Inc. publisher, New York 1972, pp. 323-448.) Also of particular relevance are methods in which fabric swatches are soiled with a soil containing a radioactive tracer element. In these cases, counting of the soiled fabric radioactivity before and after laundering provides the measure of soil removal. (See, for further description of such methods, the publications of B. E. Gordon and E. L. Bastian, J. Am. Oil Chem. Soc., vol. 45, pp. 754-759; B. E. Gordon, J. Roddewig, and W. T. Shebs, J. Am. Oil Chem. Soc., vol. 44, pp. 289-294; W. T. Shebs and B. E. Gordon, J. Am. Oil Chem. Soc., vol. 45, pp. 377-380; and B. E. Gordon and W. T. Shebs, J. Am. Oil. Chem. Soc., vol. 46, pp. 537-543.) Under conventional practice, radiolabelling of soils for detergency testing is a technique which has been applied only to non-proteinaceous oily soils and to clay soils.

SUMMARY OF THE INVENTION

The present invention provides a reliable and versatile method for determining the effectiveness of detergents in removing proteinaceous soils. According to the test method of the invention, there is prepared a proteinaceous test soil which is uniquely suited to quantitative measurement by both reflectance and radiotracer techniques.

In brief summary, this invention is a process for determining the removal of proteinaceous soil by a detergent formulation which comprises steps for (a) radiolabelling a quantity of blood hemoglobin, (b) soiling a substrate with the labelled blood hemoglobin, (c) analyzing the soiled substrate for hemoglobin content by both light reflectance measurement or radioactivity counting, (d) washing the soiled substrate with the detergent formulation, (e) analyzing the washed substrate for hemoglobin content by the same method or methods applied in step c, and (f) comparing the results of the analyses of steps c and e.

In part, the invention is found to have particular benefits attributable to the specific use made of blood as a test soil for controlled, quantitative detergency performance evaluations. Blood is easily obtainable and, for purposes of the invention, very uniform in properties and composition. Furthermore, blood is considered very representative of proteinaceous soils actually encountered in the typical practical applications of detergents. Still further, blood is uniquely suited to service in this invention. Because of its prominent reddish-brown color, blood stains and their removal can be easily assessed by light reflectance measurements. In addition, radiotracers are easily incorporated into the blood hemoglobin by established techniques.

Under the invention, the hemoglobin of the red blood cells which provides the stain which is the basis of reflectance measurements also serves as the carrier for the radioisotope which is the basis for detergency performance determination by radioactivity counting. This correspondence between the two different bases of analysis is an important factor in process flexibility and reliability. Detergency performance tests are generally characterized by a significant scatter in results, requiring replicate testing under the same test conditions. It is considered to be of particular advantage that, in certain preferred embodiments, the invention provides internal confirmation of the reliability of its results, through analysis of the effectiveness of the removal of the same soil by two independent (reflectance and radiotracer) methods. The process of the invention is particularly useful in testing and comparing the proteinaceous soil removal capabilities of enzyme containing detergent formulations.

DESCRIPTION OF THE PREFERRED EMBODIMENTS

The test method of the invention necessarily comprises four distinct aspects: treatment of red blood cells to incorporate one or more radiotracers into the hemoglobin molecule, soiling of a test substrate with the treated cell hemoglobin, washing of the test substrate with a detergent solution, and measurement of the hemoglobin content of the substrate before and after washing.

The incorporation of radiotracers into the hemoglobin of the red blood cells is suitably accomplished by any of a number of methods which are known in the medical and biological sciences. Tagging may be carried out either in vivo or in vitro. In one particularly preferred practice for in vitro tagging, freshly drawn blood (for example, human, cattle, or rabbit blood) is tagged with the chromium isotope 51. Tagging is accomplished by contacting the blood with a saline solution containing a chromium 51 compound such as, for example, $Na_2CrO_4$ or $CrCl_3$. The chromium is taken up rapidly by the red cells and is bound to the hemoglobin of the cells. Additional description of methods for chromium 51 tagging of hemoglobin is found in the following publications, the relevant teachings of which are incorporated herein by this reference: S. J. Gray and K. Sterling, *J. Clin. Investig.*, vol. 29 (1950), pp. 1604–1613; N. C. Hughes Jones and P. L. Mollison, *Clinical Science*, vol. 15 (1955), pp. 207–218; P. L. Mollison and N. Veall, *Brit. J. Haematology,* vol. 1 (1955), pp. 62–74; and M. C. Cooper and C. A. Owens, Jr., *J. Lab. Clin. Med.*, vol. 47 (1956), pp. 65–71.

A preferred method for in vivo tagging comprises direct injection into the blood source of a solution containing iron isotope 59, for instance, a solution of ferrous 59 citrate in aqueous citric acid. Suitable procedures for in vivo tagging with iron are described in more detail hereinbelow.

The particular blood cell/hemoglobin source is not critical to the invention, and in general any animal provides a suitable blood source. Preferred from the standpoint of availability are horse, cattle, swine, sheep, rabbit, and human blood. Either whole blood, or a red blood cell containing fraction of whole blood, or a hemoglobin containing extract may be used. Similarly, the particular radiotracer incorporated into the hemoglobin is not a critical aspect of the invention, although preference may be expressed for a tracer selected from the group consisting of iron atomic weight 59, chromium atomic weight 51, carbon atomic weight 14, and iodine atomic weight 125.

After tagging, the hemoglobin is applied to a substrate simulating the service for which the detergent formulation under evaluation is intended. Most advantageous use of the invention is made in the testing of laundry detergent performance. In this service, the substrate is preferably a swatch of fabric of uniform predetermined size, for example, having an area of about 5 to 50 square inches. Cotton and polyester/cotton blends are particularly preferred as representative of fabrics typically encountered in household laundry service.

Tagged hemoglobin is easily applied to the substrate surface by spraying, soaking, or the like. In the case of a fabric substrate, best results are obtained when the hemoglobin is distributed uniformly across the full surface of the swatch in an amount sufficient to moisten but not wet the surface. In other words, the total liquid applied should preferably be no more than can be naturally absorbed by the fabric. The swatches are then dried before measurement of the soil/stain by radioactivity counting and light reflectance.

Light reflectance and radioactivity measurements both before and after the substrates are washed are suitably made using conventional reflectometer and/or colorimeter techniques. As a specific example, reflectance measurements are very suitably made using the "Y" scale of the Gardner XL-23 Colorimeter (Gardner Laboratory, Bethesda, Md.). Radioactivity counting is most conveniently accomplished by procedures well known in detergency studies involving removal of other soils, for instance, the gamma counting procedures described in the above-referenced publications of Gordon et al and Shebs et al.

Washing of the soiled substrate (for instance, laundering of a soiled fabric swatch) is carried out under controlled conditions. In this regard, specific attention should be given to controlling such variables as wash water hardness, temperature, and detergent content, as well as to the extent of agitation or scrubbing action applied to the substrate.

The invention is now illustrated with reference to the following examples which illustrate specific preferred embodiments and are not intended to limit its broader scope.

EXAMPLES

A series of experiments were carried out according to the invention, involving the tagging of rabbit blood with iron 59 and the use of the tagged blood in tests of the laundry performance of enzyme containing heavy duty liquid detergent formulations.

The tagging of the hemoglobin was carried out in vivo in female New Zealand White rabbits, each weighing approximately 3 to 5 kg. Each animal was injected with approximately 0.5 ml of a dosing solution containing about 100 micro Ci (micro Curries) of iron 59 per ml. On days 5 and 7 after dosing, approximately 30 ml of whole blood was collected from each animal into citrate anticoagulant solution (prepared by dissolving 6 grams of citric acid and 16.5 grams of sodium citrate in deionized water to a total volume of 250 ml), in a proportion of about 5 ml of anticoagulant to 100 ml of blood. Collected blood was stored at 4° C. until used. Analysis of the blood showed that about 45% of the dosed radioactivity had been incorporated into the blood of the animals, and that only about 1% of the radioactivity in the blood was found in the plasma, indicating that 99% of the activity in the blood was attributable to the red blood cells. Specific activity of the whole blood collected was about 0.25 micro Ci per ml.

The iron 59 tagged blood was then used as a test soil in an investigation of the relative performance of a series of detergent formulations. The investigation was particularly directed to determining the influence on performance of the addition of small amounts of enzymes to typical detergent formulations.

For purposes of this investigation, a number of fabric swatches were soiled with the tagged rabbit blood. Strips of permanent press polyester/cotton fabric, 4 inches wide and 45 inches long, were soaked in a tray containing about 200 ml of the labeled blood. Each strip was agitated gently to thoroughly wet the fabric, removed from the tray and drawn through a pair of rollers to express excess liquid. The soaked strip was then placed on top of a clean strip, the two strips were rolled tightly together, and the roll was manually twisted and worked to transfer some of the blood to the clean strip. This procedure left both strips stained approximately equally. Next, the strips were dried at 60°–80° C. with a flow of hot air, conditioned overnight in an oven at 60° C., agitated in hot (60° C.) water for twenty minutes, rinsed and dried at room temperature. Finally the strips were cut into 4 inch squares (swatches).

Scintillation counting and reflectance measurements were made for each swatch to provide baseline data for the detergency performance tests. Scintillation counts were made with a Beckman Instruments Gamma 8000 gamma counter. Reflectance measurements were made using the "Y" scale of a Gardner XL-23 Colorimeter.

The swatches were then laundered under controlled conditions in a series of washing tests to compare the performance of a series of detergent formulations. For each washing test, two of the soiled swatches were washed at 38° C. in a solution of 0.5 gram of liquid laundry detergent in 500 ml of water containing 150 ppm of total water hardness (calculated as $CaCO_3$). The washing tests were carried out in a Terg-O-Tometer, a conventional testing device which is equipped with a beaker for containing the detergent solution and the fabric swatches and a constant-speed motor driven propeller for agitating the contents of the beaker.

These procedures were applied to the testing of four detergent formulations. Each of the four formulations was an aqueous concentrate containing 22.5 percent by weight (%w) of a nonionic surfactant, 7.5%w of an anionic surfactant, 7.0%w ethyl alcohol, between 0 and 2.0%w of a protease enzyme and the balance water. The nonionic surfactant was in each case an alcohol ethoxylate prepared by the addition of an average of about 7 mols of ethylene oxide per mol of a mixture of $C_{12}$ to $C_{15}$ alcohols. The anionic surfactant was an alkylbenzene sulfonate having a $C_{12}$ linear alkyl moiety. The four formulations differed in their content of the enzyme: the formulation designated A contained no enzyme, the formulation B contained 0.5% enzyme, the formulation C contained 1.0% enzyme, and the formulation D contained 2.0% enzyme.

Following each washing test, the fabric swatches were removed from the wash solution and air dried. Scintillation counting and reflectance measurements were carried out for each laundered swatch in the same manner as they had been for the soiled swatches. Scintillation counting results before and after washing were used to calculate soil (hemoglobin) removal during the washing, as a percentage of the soil present on the fabric before washing. Reflectance results were obtained simply as the difference in the absolute reflectance values before and after washing.

Results of the tests are presented in Table I below. As can be seen from the Table, results for soil removal determined on the basis of removal to the tagged hemoglobin are consistent with results determined on the basis of the change in reflectance of the soiled fabric swatches upon washing. The ranking of the several detergent formulations in terms of their performance is the same for both sets of results.

TABLE I

| FORMULATION | % W PROTEASE | DETERGENCY | |
| --- | --- | --- | --- |
| | | % W SOIL REMOVED[a] | $\Delta R$[b] |
| A | 0 | 26 | 2.2 |
| B | 0.5 | 29 | 4.0 |
| C | 1.0 | 31 | 4.5 |
| D | 2.0 | 34 | 5.1 |

[a] By scintillation counting $^{59}$Fe before and after washing.
[b] By reflectance measurements before and after washing.

We claim as our invention:

1. A method for determining the removal of proteinaceous soil by a detergent formulation, which comprises steps for
   a. radiolabelling a quantity of blood hemoglobin,
   b. soiling a test substrate with the labelled blood hemoglobin,
   c. analyzing the soiled substrate for hemoglobin content by both light reflectance measurement and radioactivity counting,
   d. washing the soiled substrate with the detergent formulation,
   e. analyzing the washed substrate for hemoglobin content by both light reflectance and radioactivity counting, and
   f. comparing the results of the analyses in steps c and e.

2. The method of claim 1, wherein the test substrate is one or more fabric swatches.

3. The method of claim 2, wherein the blood hemoglobin is labelled with a radioactive isotope selected from the group consisting of chromium 51 and iron 59.

4. A method for determining the removal of proteinaceous soil by an enzyme-containing detergent formulation, which comprises steps for
   a. radiolabeling a quantity of blood hemoglobin with a radioactive isotope selected from the group consisting of chromium 51 and iron 59,
   b. soiling one or more fabric swatches with the labelled blood hemoglobin,
   c. analyzing the soiled swatches for hemoglobin content by both light reflectance measurement and radioactivity counting,
   d. washing the soiled swatches with an enzyme-containing detergent formulation,
   e. analyzing the washed swatches for hemoglobin content by both light reflectance and radioactivity counting, and
   f. comparing the results of the analyses in steps c and e.

* * * * *